United States Patent [19]
Southan et al.

[11] Patent Number: 5,985,917
[45] Date of Patent: Nov. 16, 1999

[54] MERCAPTO AND SELENO DERIVATIVES AS INHIBITORS OF NITRIC OXIDE SYNTHASE

[75] Inventors: Garry J. Southan, Frederick, Md.; Andrew L. Salzman; Csaba Szabó, both of Cincinnati, Ohio

[73] Assignee: Children's Hospital Medical Center, Cincinnati, Ohio

[21] Appl. No.: 09/281,125

[22] Filed: Mar. 29, 1999

Related U.S. Application Data

[60] Division of application No. 08/545,952, Oct. 20, 1995, which is a continuation-in-part of application No. 08/410,312, Mar. 24, 1995, Pat. No. 5,674,907.

[51] Int. Cl.$^6$ .......................... A61K 31/28; A61K 31/31; A61K 31/155; A61K 31/33
[52] U.S. Cl. .......................... 514/492; 514/497; 514/183; 514/634
[58] Field of Search .................................. 514/492, 497, 514/183, 634

[56] References Cited

U.S. PATENT DOCUMENTS 5,298,506  3/1994  Stamler et al. ...................... 514/226.2

FOREIGN PATENT DOCUMENTS 547558  6/1993  European Pat. Off. .
5141873  7/1975  United Kingdom .
9412165  6/1994  WIPO .

OTHER PUBLICATIONS

Khym et al., "Ion Exchange Studies of Transguanylation Reactions. II. . . . and 2–Aminothiazolines or Penthiazolines", *Journal of the American Chemical Society*, vol. 80, pp. 3342–3349, Jul. 5, 1958.

Doherty et al., "Synthesis of D– and L–2–Aminobutylisothiourea Dihydrobromide Isomers and their Conversion to Guanidothiols, Disulphides, and Thiazolines", *Journal of Organic Chemistry*, vol. 28, pp. 1339–1342, 1963.

*Chemical Abstracts*, vol. 82, 1975, p. 12, #164694y, Tumor rejection in experimental animals treated with radioprotective thiols.

*Cancer Research*, 35. 429–437., Feb. 1975, Tumor Rejection in Experimental Animals Treated with Radioprotective Thiols.

Szabó et al., "Beneficial effects and improved survival in rodent models . . . nitric oxide synthase", *Pharmacology*, vol. 91, pp. 12472–12476. Dec. 1994.

Southan et al., "Isothioureas: potent inhibitors of nitric oxide synthases . . . selectivity", *British Journal of Pharmacology*, vol. 114, pp. 510–516, 1995.

Wu et al., "Aminoguanidine attenuates the delayed circulatory failure and . . . shock" *British Journal of Pharmacology*, vol. 113, pp. 001–007, Paper No. 78594, 1994.

Khym et al., "Ion Exchange Studies of Transguanylation Reactions. I. Rearrangement of S,2–Aminoethylisothiourea . . . Aminothiazoline", *Journal of the American Chemical Society*, vol. 79, pp. 5663–5666, Nov. 5, 1957.

Doherty et al., "Synthesis of Aminoalkylisothiuronium Salts and their Conversion to Mercaptoalkylguanidines and Thiazolines", *Journal of the American Chemical Society*, vol. 79, pp. 5667–5671, Nov. 5, 1957.

Chu, S., et al., "Potential Antiradiation Agents. II. Selenium Analogs of 2–Aminoethylisothiouronium Hydrobromide and Related Compounds," *Journal of the American Chemical Society*, vol. 27, pp. 2899–2901, Aug. 1962.

Hino, T., et al., "Radiation–protective Agents. I. Sutdies on N–Alkylated–2–(2–aminoethyl)thiopseudoureas and 1,1–(Dithioethylene)diguanidines", *Chemical & Pharmaceutical Bulletin*, vol. 14, No. 11, pp. 1193–1201, Nov. 1966.

*Primary Examiner*—Theodore J. Criares
*Attorney, Agent, or Firm*—Wood, Herron & Evans, L.L.P.

[57] ABSTRACT

This invention is directed to a pharmacologically acceptable composition for inhibiting nitric oxide synthase in a mammal, which includes a mercapto or seleno derivative and a pharmaceutically acceptable carrier. The invention also concerns a method of inhibiting nitric oxide synthase, selectively inhibiting the inducible isoform of nitric oxide synthase, and treating various conditions where there is an advantage in inhibiting nitric oxide biosynthesis. The method includes the step of administering to a mammal a mercapto or seleno derivative in pure form or in a pharmaceutically acceptable carrier.

26 Claims, 5 Drawing Sheets

MERCAPTO AND SELENO DERIVATIVES AS INHIBITORS OF NITRIC OXIDE SYNTHASE

RELATED APPLICATION

This application is a division of application Ser. No. 08/545,952 filed Oct. 20, 1995, pending, which is a continuation in part of application Ser. No. 08/410,312 entitled "MERCAPTO DERIVATIVES AS INHIBITORS OF NITRIC OXIDE SYNTHASE" filed on Mar. 24, 1995, which is incorporated herein in its entirety by reference now U.S. Pat. No. 5,674,907.

BACKGROUND OF THE INVENTION

The present invention relates to the use of mercapto and seleno derivatives as inhibitors of nitric oxide synthase (NOS).

The free radical nitric oxide (NO) is synthesized from the guanidino group of L-arginine by a family of enzymes termed nitric oxide synthase (NOS). The brain isoform (bNOS) is constitutively present in the neural tissue and NO is released as a neurotransmitter by activation of various (e.g. NMDA-type) receptors. NO in the central nervous system plays an important role in the genesis of memory.

The continuous release of NO from the constitutive endothelial isoform of NOS (ecNOS) keeps the vasculature in a continuous state of active vasodilatation and reduces the adhesion of platelets and polymorphonuclear granulocytes (PMNs) to the endothelial surface. The biological activity of NO from the ecNOS was originally described as endothelium-derived relaxing factor (EDRF). The release of EDRF in vivo and in vitro is stimulated by shear stress and various hormones and autocoids such as acetylcholine, bradykinin, substance P. vasopressin, noradrenaline, histamine or platelet-activating factor.

The inducible isoform of NOS (iNOS) is expressed in response to immunological stimuli in multiple cell types including macrophages, vascular smooth muscle cells and epithelial cells, and produces large amounts of NO (nanomoles of NO rather than picomoles of NO derived by the ecNOS or bNOS). NO in high local concentrations can act as a cytostatic and cytotoxic molecule acting against fungal, bacterial, helminthic and protozoal antigens as well as tumor cells. A number of pro-inflammatory cytokines and endotoxin (bacterial lipopolysaccharide, LPS) also induce the expression of iNOS in a number of other cells, including fibroblasts, glial cells, cardiac myocytes as well as vascular and non-vascular smooth muscle cells.

There is now substantial evidence that iNOS plays an important role in the pathogenesis of a variety of diseases. Circulatory shock of various etiologies is associated with profound changes in the body's NO homeostasis. In animal models of endotoxic shock, endotoxin produces an acute release of NO from the constitutive isoform of nitric oxide synthase in the early phase, which is followed by induction of iNOS. In addition, it is now thought that excess NO production may be involved in a number of conditions, including conditions that involve systemic hypotension such as septic (toxic) shock and therapy with certain cytokines. Therefore, it is desirable to inhibit nitric oxide synthase. Furthermore, because of the potentially serious consequences of over-inhibition of the constitutive NOS enzyme, it is preferred to selectively inhibit the inducible isoform. Over-inhibition of the constitutive isoform may lead to hypertension, thrombosis, central nervous system toxicity and tissue damage.

Various nitric oxides synthase inhibitors have been proposed for therapeutic use. For example, NG-methyl-L-arginine (L-NMA) and NG-nitro-L-arginine methyl ester (L-NAME) have been suggested. However, they are generally nonselective in that they inhibit both the constitutive and the inducible NOS isoforms to a similar extent. Other NOS inhibitors proposed for therapeutic use include isothiourea derivatives and aminoguanidine. In in vitro and in vivo tests, isothioureas have been shown to inhibit NOS activity, and a few specific compounds within the class of isothioureas have been shown to be relatively selective inhibitors of iNOS activity (see, for example, Garry J. Southan et al., "Isothioureas: Potent Inhibitors of Nitric Oxide Synthases with Variable Isoform Selectivity", British Journal of Pharmacology, Vol. 114, pp. 510–516, 1995; Csaba Szabó et al., "Beneficial Effects and Improved Survival in Rodent Models of Septic Shock with S-methylisothiourea Sulfate, a Potent and Selective Inhibitor of Inducible Nitric Oxide Synthase", Proc Natl Acad Sci USA, Vol. 91, pp. 12472–12476 (December 1994); and PCT Application No. WO 94/12165). Aminoguanidine also has been found to selectively inhibit the inducible isoform of nitric oxide synthase in various in vitro and in vivo models (see, for example, Chin-Chen Wu et al., "Aminoguanidine Attenuates the Delayed Circulatory Failure and Improves Survival in Rodent Models of Endotoxic Shock", British Journal of Pharmacology, Vol. 113, pp. 001–007, Paper No. 78594 (1995); and European Patent Application 0 547 558 A1).

Although the nitric oxide synthase inhibitors discussed above may prove to have therapeutic use, it is important to identify additional compounds which inhibit nitric oxide synthase. It also is desirable to identify additional compounds which selectively inhibit the inducible isoform of the NOS enzyme. Because excess nitric oxide production plays such a role in a number of different disorders and conditions, such as systemic hypotension, septic shock and cytokine therapy, for example, it is extremely important to identify additional compounds capable of inhibiting, and even selectively inhibiting, nitric oxide synthase. This is especially true given that such additional compounds may prove to have fewer side effects and greater selectivity in inhibiting the inducible nitric oxide synthase enzymes.

SUMMARY OF THE INVENTION

This invention is directed to a pharmacologically acceptable composition for inhibiting nitric oxide synthase in a mammal. The composition includes a mercapto or seleno derivative and a pharmaceutically acceptable carrier, with the mercapto or seleno derivative present in the composition in an effective amount to inhibit nitric oxide synthase in the mammal.

The invention also is directed to a method of inhibiting nitric oxide synthase in a mammal, which includes the step of administering to the mammal a mercapto or seleno derivative in a pure form or in a pharmaceutically acceptable carrier.

The mercapto or seleno derivative of the composition and method is defined by a formula selected from the group consisting of:

and

-continued or a salt thereof, wherein $R_1$ is H, alkyl, alkenyl, phenyl, alkylene, alkenylene, or phenylalkylene or a substituted derivative thereof;

When $R_1$ is alkylene or alkenylene, $R_1$ optionally may be joined to either of the amidino Ns, to Z or to X of the above formula containing $R_1$ to form a 5-, 6- or 7-membered heterocyclic ring, with the proviso that when $R_1$ is attached to Z, Z is alkylene or alkenylene or a substituted derivative thereof, and, when $R_1$ is attached to X, X is either $CR_5$ or N;

$R_2$, $R_3$, $R'_2$ and $R'_3$ are independently H, lower alkyl, alkenyl, alkylene, alkenylene, amino, phenyl or phenylalkylene, or a substituted derivative thereof;

When $R_2$ or $R'_2$ is alkylene or alkenylene, $R_2$ or $R'_2$ optionally may be joined to the imino N residing on the adjacent amidino C to form a 5- or 6-membered heterocyclic ring;

Z and Z' are independently alkylene, alkenylene, cycloalkylene or cycloalkenylene, or a substituted derivative thereof;

When $R_2$, $R_3$, $R'_2$ or $R'_3$ is alkylene or alkenylene, $R_2$, $R_3$, $R'_2$ or $R'_3$ optionally may be joined to the adjacent Z or Z' to form a 5- or 6-membered heterocyclic ring including N, C and not more than one atom of O or S, with the proviso that said heterocyclic ring optionally being substituted with a lower alkyl, alkoxy, halo, hydroxy or amino;

X is N, $NR_4$, O, $CR_5$ or $CR_4R_5$;

X' is N, $NR'_4$, O, $CR'_5$ or $CR'_4R'_5$;

Y is S or Se;

$R_4$ and $R'_4$ are independently H, alkyl, thioalkylene or thioesteralkylene;

$R_5$ and $R'_5$ are independently H, alkyl, alkylene, alkenylene, thioalkylene, thioesteralkylene, amino or carboxyl; and When $R_4$ or $R'_4$ is alkylene, alkenylene, thioalkylene, or thioesteralkylene, $R_4$ or $R'_4$ optionally may be joined to $R_2$, $R_3$, $R'_2$ or $R'_3$ to form a 5- or 6-membered heterocyclic ring including N, C and not more than one atom of O or S, with the proviso that $R_2$, $R_3$, $R'_2$ and $R'_3$ are independently alkylene, alkenylene, amino, phenyl, phenylalkylene, or a substituted derivative thereof wherein the substituted derivative is lower alkyl or halo.

DETAILED DESCRIPTION OF THE INVENTION

This invention is directed to a pharmacologically acceptable composition for inhibiting nitric oxide synthase in a mammal. The composition includes a mercapto or seleno derivative and a pharmaceutically acceptable carrier, with the mercapto or seleno derivative present in the composition in an effective amount to inhibit nitric oxide synthase in the mammal. The invention also is directed to a method of inhibiting nitric oxide synthase in a mammal, which includes the step of administering to the mammal a mercapto or seleno derivative in pure form or in a pharmaceutically acceptable carrier.

Suitable mercapto or seleno derivatives for use in the composition or method may be made according to the methods of synthesis taught in the following articles which are incorporated herein in their entirety by reference:

(1) Joseph X. Khym et al., "Ion Exchange Studies of Transguanylation Reactions. I. Rearrangement of S,2-Aminoethylisothiourea to 2-Mercaptoethylguanidine and 2-Aminothiazoline", *Journal of the American Chemical Society*, Vol. 79, pp 5663–5666, Nov. 5, 1957;

(2) David G. Doherty, et al., "Synthesis of Aminoalkylisothiuronium Salts and their Conversion to Mercaptoalkylguanidines and Thiazolines", *Journal of the American Chemical Society*, Vol. 79, pp 5667–5671, Nov. 5, 1957;

(3) Joseph X. Khym, et al., "Ion Exchange Studies of Transguanylation Reactions. II. Rearrangement of 3-Aminopropylisothiourea and N-Substituted Aminoethyl- and Aminopropylisothioureas to Mercaptoalkylguanidines and 2-Aminothiazolines or Penthiazolines", *Journal of the American Chemical Society*, Vol. 80, pp 3342–3349, Jul. 5, 1958;

(4) David G. Doherty et al. "Synthesis of D- and L-2-Aminobutylisothiourea Dihydrobromide Isomers and their Conversion to Guanidothiols, Disulfides, and Thiazolines", *Journal of Organic Chemistry*, Vol. 28, pp 1339–1342, 1963.

(5) Shih-Hsi Chu et al., "Potential Antiradiation Agents. II. Selenium Analogs of 2-Aminoethylisothiouronium Hydrobromide and Related Compounds", *Journal of the American Chemical Society*, Vol. 27, pp 2899–2901, August, 1962.

(6) Tohru Hino et al., "Radiation-protective Agents. I. Studies on N-Alkylated-2-(2-aminoethyl) thiopseudoureas and 1,1-(Dithioethylene) diguanidines", *Chemical & Pharmaceutical Bulletin*, Vol. 14, No. 11, pp. 1193–1201, November, 1966.

Suitable mercapto derivatives also may be made according to the examples provided at the end of this detailed description of the invention.

The mercapto or seleno derivative of the composition and method is defined by a formula selected from the group consisting of:

and or a salt thereof, wherein $R_1$ is H, alkyl, alkenyl, phenyl, alkylene, alkenylene, or phenylalkylene or a substituted derivative thereof;

When $R_1$ is alkylene or alkenylene, $R_1$ optionally may be joined to either of the amidino Ns, to Z or to X of the above formula containing $R_1$ to form a 5-, 6- or 7-membered heterocyclic ring, with the proviso that when $R_1$ is attached to Z, Z is alkylene or alkenylene or a substituted derivative thereof, and, when $R_1$ is attached to X, X is either $CR_5$ or N;

$R_2$, $R_3$, $R'_2$ and $R'_3$ are independently H, lower alkyl, alkenyl, alkylene, alkenylene, amino, phenyl or phenylalkylene, or a substituted derivative thereof;

When $R_2$ or $R'_2$ is alkylene or alkenylene, $R_2$ or $R'_2$ optionally may be joined to the imino N residing on the adjacent amidino C to form a 5- or 6-membered heterocyclic ring;

Z and Z' are independently alkylene, alkenylene, cycloalkylene or cycloalkenylene, or a substituted derivative thereof;

When $R_2$, $R_3$, $R'_2$ or $R'_3$ is alkylene or alkenylene, $R_2$, $R_3$, $R'_2$ or $R'_3$ optionally may be joined to the adjacent Z or Z' to form a 5- or 6-membered heterocyclic ring including N, C and not more than one atom of O or S, with the proviso that said heterocyclic ring optionally being substituted with a lower alkyl, alkoxy, halo, hydroxy or amino;

X is N, $NR_4$, O, $CR_5$ or $CR_4R_5$;

X' is N, $NR'_4$, O, $CR'_5$ or $CR'_4R'_5$;

Y is S or Se;

$R_4$ and $R'_4$ are independently H, alkyl, thioalkylene or thioesteralkylene;

$R_5$ and $R'_5$ are independently H, alkyl, alkylene, alkenylene, thioalkylene, thioesteralkylene, amino or carboxyl; and When $R_4$ or R'4 is alkylene, alkenylene, thioalkylene, or thioesteralkylene, $R_4$ or $R'_4$ optionally may be joined to $R_2$, $R_3$, $R'_2$ or $R'_3$ to form a 5- or 6-membered heterocyclic ring including N, C and not more than one atom of O or S, with the proviso that $R_2$, $R_3$, $R'_2$ and $R'_3$ are independently alkylene, alkenylene, amino, phenyl, phenylalkylene, or a substituted derivative thereof wherein the substituted derivative is lower alkyl or halo.

As used herein, the term "salt" refers to any addition salt derived from any pharmaceutically acceptable organic or inorganic acid. Examples of suitable acids include hydrochloric, hydrobromic, sulfuric, nitric, perchloric, fumaric, maleic, phosphoric, glycolic, lactic, salicylic, succinic, toluene p sulfonic, tartaric, acetic, citric, methanesulfonic, formic, benzoic, malonic, naphthalene-2-sulfonic and benzenesulphonic acids. Additionally, as used herein, any alkyl or alkylene may be straight chain, branched or cyclic, and "halo" includes bromine, chlorine, fluorine and iodine.

As mentioned above, $R_1$ is H, alkyl, alkenyl, phenyl, alkylene, alkenylene or phenylalkylene, or a substituted derivative thereof. If desired, this $R_1$ derivative may be substituted with one or more alkoxy, halo, hydroxy, amino or nitro groups. Additionally, as noted above, $R_2$, $R_3$, $R'_2$ and $R'_3$ are independently H, lower alkyl, alkenyl, alkylene, alkenylene, amino, phenyl or phenylalkylene, or a substituted derivative thereof. If desired, the $R_2$, $R_3$, $R'_2$ and $R'_3$ derivative may be substituted with a lower alkyl or halo.

If the $R_4$, $R_5$, $R'_4$ or $R'_5$ substituent is thioalkylene, the thioalkylene preferably has a formula $[-(CH_2)_n-SH]$ where n is independently 1 to 4. If $R_4$, $R_5$, $R'_4$ or $R'_5$ is thioesteralkylene, the thioesteralkylene preferably has the formula $[-(CH_2)_n-S-R_6]$ where $R_6$ is independently a lower alkyl and n is independently 1 to 4.

The Z and Z' substituents of the mercapto or seleno derivative are independently alkylene, alkenlyene, cycloalkyene or cycloalkenylene, or a substituted derivative thereof. When such a substituted derivative is employed, the substituent may include an alkoxy, halo, hydroxy, amino or nitro group.

A preferred subgroup of the mercapto or seleno derivative includes mercapto or seleno derivatives where: $R_1$ is H or lower alkyl; $R_2$ is H; $R_3$ is H; $R'_2$ is H; $R'_3$ is H; X is $NR_4$; X' is $NR'_4$; $R_4$ and $R'_4$ are independently H, methyl or ethyl; and Z and Z' are independently alkylene. A few nonlimiting examples include mercaptoethylguanidine, mercaptopropylguanidine, S-methyl-mercaptoethylguanidine, S-methyl-mercaptopropylguanidine, selenoethylguanidine, selenopropylguanidine and guanidinoethyldisulfide. Another preferred subgroup of mercapto or seleno derivatives is formed wherein: $R_1$ is H; $R_2$ is H; $R_3$ is H; $R'_2$ is H; $R'_3$ is H; X is $NR_4$; X' is $NR'_4$; $R_4$ is H; $R'_4$ is H; and Z and Z' are independently a $C_{1-6}$ alkylene. Nonlimiting examples include mercaptoethylguanidine, mercaptopropylguanidine, selenoethylguanidine, selenopropylguanidine and guanidinoethyldisulfide.

In addition to the mercapto and seleno derivatives discussed above, if desired, the seleno derivative of the composition and method may be an isoselenourea. Isoselenoureas have the general formula:

Nonlimiting examples of isoselenoureas include aminoethylisoselenourea (AE-SeU), aminopropylisoselenourea (AP-SeU) and 2-aminoselenazoline (ASeZ).

AE-SeU and AP-SeU may exert their NOS inhibitory effect through intramolecular rearrangement to yield selenoethylguanidine (SEG) and selenopropylguanidine (SPG), respectively. In tests with these isoselenourea compounds, solutions of either compound caused the reduction of "Aldrithiol-2" (2,2'-dithiopyridine, 2-dipyridyl disulfide), a reagent used to measure free thiol (—SH) and free selenol (—SeH) groups. This reduction was rapid at neutral pH, but slower at lower pH values. Furthermore, the concentrations of AE-SeU and AP-SeU in solution, as measured by high pressure liquid chromatography (HPLC), diminished at rates that were similarly pH dependent. These data suggest that AE-SeU and AP-SeU rearrange to yield other species predominantly selenoalkylguanidines, in accord with data by Chu and Mautner (S. H. Chu and H. G. Mautner, *Journal of the American Chemical Society*, 27, 2899–2901 (1962).

The mercapto or seleno derivative, in pure form or in a pharmaceutically acceptable carrier, will find benefit in treating conditions and disorders where there is an advantage in inhibiting the nitric oxide synthase enzyme and selectively inhibiting the inducible isoform. For example, the mercapto or seleno derivative may be used to treat a circulatory shock including its various aspects such as vascular and myocardial dysfunction, metabolic failure including the inhibition of mitochondrial enzymes and cytochrome P450-mediated drug metabolism, and multiple organ dysfunction syndrome including adult respiratory distress syndrome. Circulatory shock may be a result of gram-negative and gram positive sepsis, trauma, hemorrhage, burn injury, anaphylaxis, cytokine immunotherapy, liver failure, kidney failure or systemic inflammatory response syndrome. Mercapto and seleno derivatives also may be beneficial for patients receiving therapy with cytokines such as TNF, IL-1 and IL-2 or therapy with cytokine-inducing agents, or as an adjuvant to short term immunosuppression in transplant therapy. In addition, mercapto and seleno derivatives may be useful to inhibit NO synthesis in patients suffering from inflammatory conditions in which an excess of NO contributes to the pathophysiology of the condition, such as adult respiratory distress syndrome (ARDS) and myocarditis, for example.

There is also evidence that an NO synthase enzyme may be involved in the pathophysiology of autoimmune and/or inflammatory conditions such as arthritis, rheumatoid arthritis and systemic lupus erythematosus (SLE) and in insulin-dependent diabetes mellitus, and therefore, mercapto and seleno derivatives may prove helpful in treating these conditions.

Furthermore, it is now clear that there are a number of additional inflammatory and noninflammatory diseases that are associated with NO overproduction. Examples of such physiological disorders include: inflammatory bowel diseases such as ileitis, ulcerative colitis and Crohn's disease; inflammatory lung disorders such as asthma and chronic obstructive airway disease; inflammatory disorders of the eye including corneal dystrophy, trachoma, onchocerciasis, uveitis, sympathetic ophthalmitis and endophthalmitis; chronic inflammatory disorders of the gum including periodontitis; chronic inflammatory disorders of the joints including arthritis and osteoarthritis, tuberculosis, leprosy, glomerulonephritis sarcoid, and nephrosis; disorders of the skin including sclerodermatitis, psoriasis and eczema; inflammatory diseases of the central nervous system, including chronic demyelinating diseases such as multiple sclerosis, dementia including AIDS-related neurodegeneration and Alzheimer's disease, encephalomyelitis and viral or autoimmune encephalitis; autoimmune diseases including immune-complex vasculitis, systemic lupus and erythematodes; and disease of the heart including ischemic heart disease and cardiomyopathy. Additional diseases which may benefit from the use of mercapto and seleno derivatives include adrenal insufficiency; hypercholesterolemia; atherosclerosis; bone disease associated with increased bone resorption, e.g., osteoporosis, pre-eclampsia, eclampsia, uremic complications; chronic liver failure, noninflammatory diseases of the central nervous system (CNS) including stroke and cerebral ischemia; and various forms of cancer.

Pharmaceutical formulations of the mercapto and seleno derivative may include those suitable for oral, rectal, nasal, topical (including buccal and sub-lingual), vaginal or parenteral (including intramuscular, sub-cutaneous and intravenous) administration, or for administration by inhalation or insufflation. The formulations may, where appropriate, be conveniently presented in discrete dosage units and may be prepared by any of the methods well known in the art of pharmacy. All such pharmacy methods include the steps of bringing into association the active compound with liquid carriers or finely divided solid carriers or both as needed and then, if necessary, shaping the product into the desired formulation.

Pharmaceutical formulations suitable for oral administration may conveniently be presented: as discrete units, such as capsules, cachets or tablets, each containing a predetermined amount of the active ingredient; as a powder or granules; or as a solution, a suspension or as an emulsion. The active ingredient may also be presented as a bolus electuary or paste, and be in a pure form, i.e., without a carrier. Tablets and capsules for oral administration may contain conventional excipients such as binding agents, fillers, lubricants, disintegrant or wetting agents. A tablet may be made by compression or molding, optionally with one or more accessory ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the active ingredient therein.

Formulations for parenteral administration include: aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use.

Alternatively, the formulations may be presented for continuous infusion. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges, comprising the active ingredient in a flavored base such as sucrose and acacia or tragacanth, and pastilles comprising the active ingredient in a base such as gelatin and glycerin or sucrose and acacia. For intra-nasal administration the compounds of the invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation the compounds according to the invention are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

When desired the above described formulations, adapted to give sustained release of the active ingredient, may be employed. The pharmaceutical compositions according to the invention may also contain other active ingredients such as antimicrobial agents, immunosuppressants or preservatives.

The compounds of the invention may also be used in combination with other therapeutic agents, for example, anti-inflammatory agents, particularly non-steroidal anti-inflammatory drugs (NSAIDs), vasodilator prostaglandins including prostacyclin and prostaglandin $E_1$, cancer chemotherapeutic agents including cisplatin, NO donors or NO inhalation therapy, or PAF—receptor antagonists.

It should be understood that in addition to the ingredients particularly mentioned above, the formulations of this invention may include other agents conventional in the art having regard to the type of formulation in question, for example, those suitable for oral administration may include flavoring agents.

Preferred unit dosage formulations are those containing an effective dose, as recited below, or an appropriate fraction thereof, of the active ingredient.

For each of the aforementioned conditions, the mercapto or seleno derivative may be administered orally or via injection at a dose of from 0.1 to 250 mg/kg per day. The dose range for adult humans is generally from 5 mg to 17.5 g/day, preferably 5 mg to 10 g/day and most preferably 100 mg to 3 g/day. Tablets or other forms of presentation provided in discrete units may conveniently contain an amount which is effective at such dosage or as a multiple of the same, for instance, units containing 5 mg to 500 mg, usually around 100 mg to 500 mg.

The pharmaceutical composition preferably is administered orally or by injection (intravenous or subcutaneous), and the precise amount administered to a patient will be the responsibility of the attendant physician. However, the dose employed will depend upon a number of factors, including the age and sex of the patient, the precise disorder being treated, and its severity. Also the route of administration may vary depending upon the condition and its severity.

The following Examples are provided by way of illustration, and are not intended to limit the scope of the invention.

EXAMPLE 1

This example illustrates the effect of selected mercapto derivatives on endotoxin-induced nitrite formation in J774.2 macrophages and on IL-1 gamma-interferon induced nitrite formation in cultured rat aortic smooth muscle cells. J774 macrophage cell lines were obtained from the American Type Culture Collection (ATCC) and were grown using standard methods in Dulbecco's Modified Eagle Medium (DMEM) supplemented with 10% fetal bovine serum, glutamine, penicillin (10,000 U/I) and streptomycin (10,000 U/I). Rat aortic smooth muscle cells (RASM) from Wistar rats were isolated by enzymatic dissociation using standard methods. The cells were positively identified as smooth muscle by indirect immunofluorescent staining for $\alpha$-actin, using mouse anti-$\alpha$-actin antibody and anti-mouse IgG fluorescein isothiocyanate (FITC) conjugate. RASM cells were grown in T-75 tissue culture flasks in 50% F12 nutrient medium and 50% Dulbecco's Modified Eagle Medium supplemented with 10% fetal bovine serum, glutamine, penicillin (10,000 U/I) and streptomycin (10,000 U/I). Cells were grown in 96-well plates for measure of nitrite production and cell viability. J774 macrophages were treated with endotoxin (10 $\mu$g/ml) for 24 hours; smooth muscle cells were treated with IL-1 (100 U/ml) and gamma-interferon (50 U/ml) for 48 hours.

Concentration of nitrite, the degradation product of NO in the culture medium, was determined by mixing equal volumes of medium with the Griess reagent (1% sulfanilamide 0.1% naphtylethylenediamine dihydrochloride/2.5% $H_3PO_4$). The mixture was incubated for 10 minutes at room temperature to form the chromophore, then optical densities (OD) were determined at 550 nm ($OD_{550}$). $NaNO_2$ was used as the standard. Spectrophotometric measurements were performed in a dual-wavelength spectrophotometer.

Mitochondrial respiration, an indicator of cell viability, was assessed by the mitochondrial-dependent reduction of MTT [3-(4,5-dimethylthiazol-2-yl) -2,5-diphenyltetrazolium bromide] to formazan. Cells in 96-well plates were incubated (37° C.) with MTT (0.2 mg/ml for 60 minutes). Culture medium was removed by aspiration and the cells solubilized in dimethylsulfoxide (DMSO) (100 $\mu$l). The extent of reduction of MTT to formazan within cells was quantitated by measurement of $OD_{550}$ using a microplate reader. The calibration curve for the reduction of MTT to formazan was prepared in DMSO. Formazan production by cells was expressed as a percentage of the values obtained from untreated cells.

Figure 1:
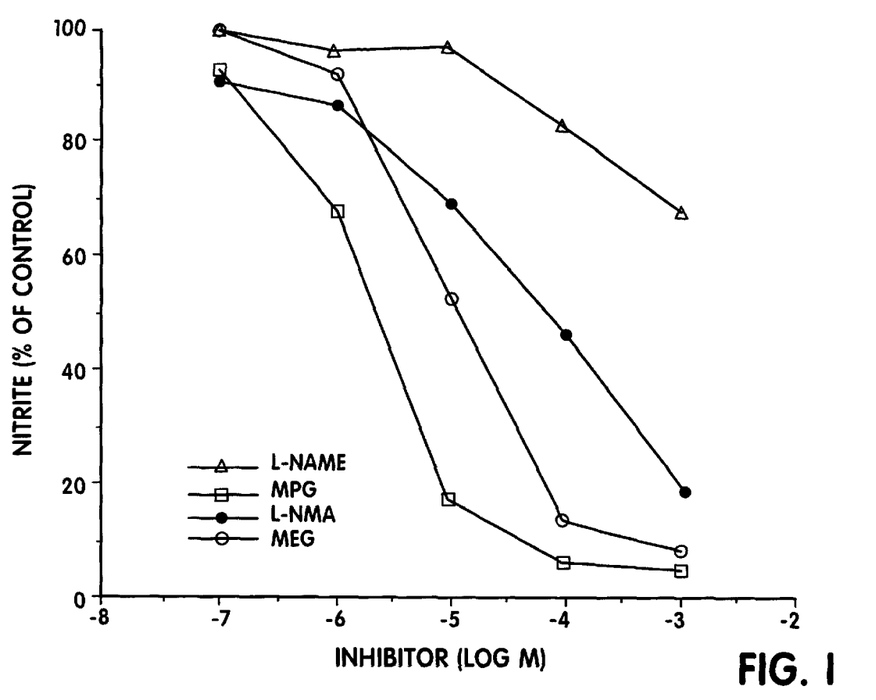
FIG. 1 is a graph of the effect of mercaptoethylguanidine (MEG), mercaptopropylguanidine (MPG), NG-methyl-L-arginine (L-NMA) and NG-nitro-L-arginine methyl ester (L-NAME) on nitrite production by immunostimulated J774 macrophages (N=3–6)
Figure 2:
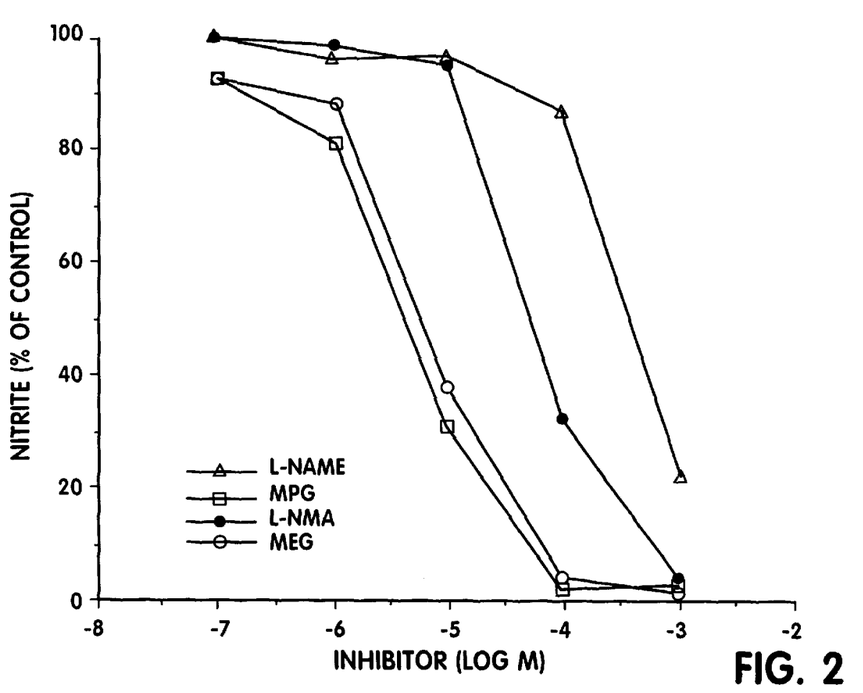
FIG. 2 is a graph of the effect of mercaptoethylguanidine (MEG), mercaptopropylguanidine (MPG), NG-methyl-L-arginine (L-NMA) and NG-nitro-L-arginine methyl ester (L-NAME) on nitrite production by immunostimulated vascular smooth muscle cells (N=3–6)
Figure 3:
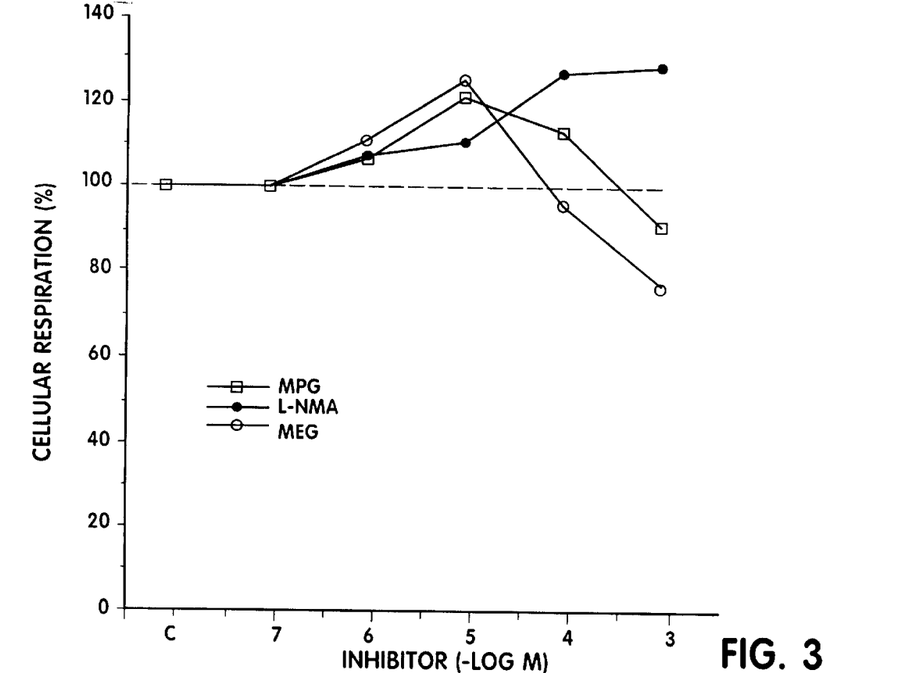
FIG. 3 is a graph of the effect of mercaptoethylguanidine (MEG), mercaptopropylguanidine (MPG), and NG-methyl-L-arginine (L-NMA) on cellular respiration by immunostimulated J774 macrophages (N=3–6) with 100% representing the activity in control samples, i.e., in the absence of any inhibitors.
Figure 4:
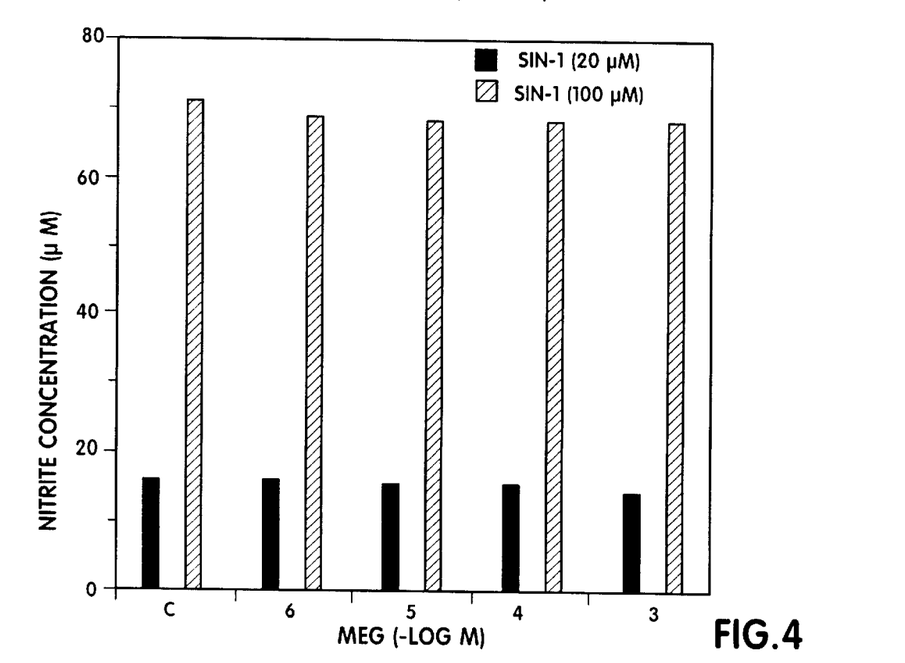
FIG. 4 is a graph of the effect of mercaptoethylguanidine (MEG) on nitrite production by the NO donor compound SIN-1 in culture medium containing 10% fetal calf serum (N=3) with "C" representing the activity in control samples, i.e., in the absence of any inhibitors.

Cells stimulated with endotoxin or with IL-1 and gamma-interferon produced nitric oxide, measured as an increase in nitrite concentration in the culture medium. This was dose-dependently inhibited by the mercapto derivatives, mercaptoethylguanidine (MEG) and mercaptopropylguanidine (MPG), which were substantially more potent inhibitors than the reference compounds NG-methyl-L-arginine (L-NMA) and NG-nitro-L-arginine methyl ester (L-NAME), as seen in FIGS. 1 and 2 and Tables 1 & 2. The inhibition of nitrite production was not due to cell killing, as these agents in their effective doses (1–100 $\mu$M) did not decrease cellular viability (FIG. 3). At 1 mM, a slight reduction in viability was observed (FIG. 3). Moreover, these agents did not scavenge nitrite or nitric oxide, as they did not interfere with the measured nitrite levels after incubation in the presence of the NO donor compound 3-morpholino-sydnonimin-hydrochloride (SIN-1) (FIG. 4). Similar to MEG and MPG, S-methyl-MEG and S-ethyl-MEG were inhibitors of nitrite accumulation in immuno-stimulated J774 macrophages (Table 1).

In this particular example, Male Wistar rats were anesthetized with thiopentone sodium (120 mg/kg, i.p). The trachea was cannulated to facilitate respiration and the rectal temperature was maintained at 37° C. by means of a rectal probe connected to a homeothermic blanket. The right carotid artery was cannulated and connected to a pressure transducer for the measurement of phasic and mean arterial blood pressure and heart rate. The left and right femoral veins were cannulated for the administration of drugs.

The mercapto derivatives MEG and MPG and reference compound L-NMA were administered in appropriate doses

TABLE 1

$EC_{50}$ values for the inhibition of nitrite production by stimulated J774 macrophages by various NOS inhibitors.

| | Compound | X | R | R' | R" | $EC_{50}$ ($\mu$M) |
|---|---|---|---|---|---|---|
| 1 | $N^G$-Methyl-L-arginine (L-NMA) | NH | —$(CH_2)_3(CH)(NH_2)CO_2H$ | —$CH_3$ | H | 159 |
| 2 | $N^G$-Nitro-L-arginine (L-NA) | NH | —$(CH_2)_3CH(NH_2)CO_2H$ | —$NO_2$ | H | –1000 |
| 3 | Aminoguanidine | NH | —$NH_2$ | H | H | 120 |
| 4 | Mercaptoethylguanidine (MEG) | NH | —$CH_2CH_2SH$ | H | H | 13 |
| 5 | Mercaptopropylguanidine (MPG) | NH | —$CH_2CH_2CH_2SH$ | H | H | 15 |
| 6 | S-methyl-MEG | NH | —$CH_2CH_2SCH_3$ | H | H | 80 |
| 7 | S-ethyl-MEG | NH | —$CH_2CH_2SCH_2CH_3$ | H | H | 328 |
| 8 | guanidylethylenedisulfide (GED) | NH | < > | H | H | 1 |

< >, R = —$(CH_2)_2SS(CH_2)_2NHC(=NH)NH_2$

TABLE 2

$EC_{50}$ values of AATUs, MAGs and other compounds for their inhibition of the activites of iNOS, ecNOS, bNOS in tissue homogenates.

| | | $EC_{50}$ ($\mu$M) | | |
|---|---|---|---|---|
| | Compound | iNOS | ecNOS | bNOS |
| 1 | $N^G$-Methyl-L-arginine (L-NMA) | 17 | 5 | 20 |
| 2 | $N^G$-Nitro-L-arginine (L-NA) | 300 | 2 | 0.8 |
| 3 | Aminoguanidine | 80 | 2600 | 220 |
| 4 | Mercaptoethylguanidine (MEG) | 11.5 | 110 | 60 |
| 5 | Mercaptopropylguanidine (MPG) | 7 | 4 | 80 |
| 6 | S-methyl-MEG | 1.4 | 43 | 8 |
| 7 | S-ethyl-MEG | 30 | 850 | 460 |
| 8 | guanidylethylenedisulfide (GED) | 200 | 630 | 180 |

EXAMPLE 2

Figure 5:
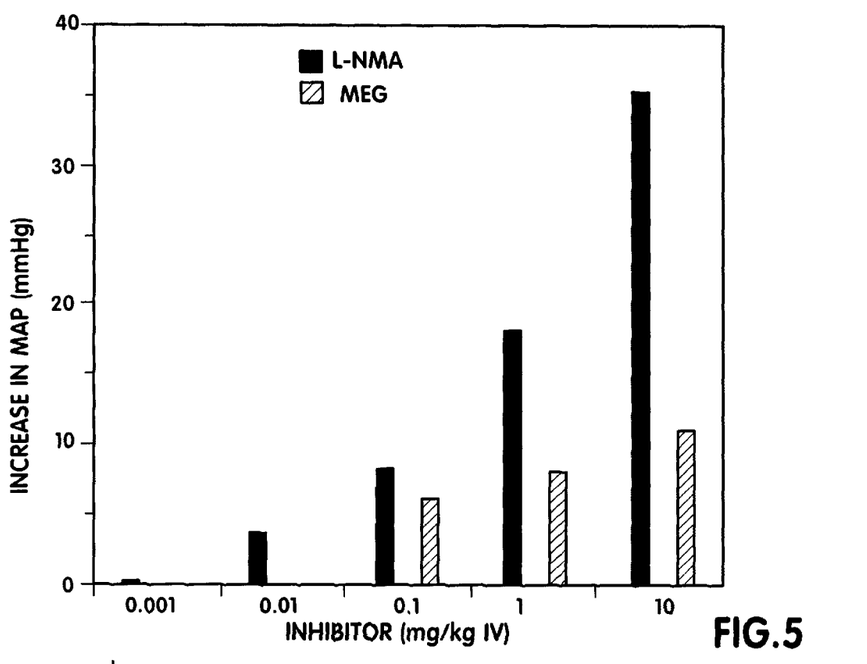
FIG. 5 is a graph of the effect of mercaptoethylguanidine (MEG) and NG-methyl-L-arginine (L-NMA) on mean arterial blood pressure (MAP) in anaesthetized rats (N=3–5)

This example illustrates the effect of selected mercapto derivatives on blood pressure in normal anesthetized rats. An increase in blood pressure by agents that inhibit NOS is a good measure of their inhibitory effect on the constitutive, endothelial NOS (ecNOS). Because L-NMA is known to be only weakly selective for inducible NOS (iNOS), inhibiting iNOS and ecNOS to a substantially similar degree, L-NMA is useful as a reference compound in illustrating isoform selectivity. If a NOS-inhibiting agent increases blood pressure less strongly than L-NMA, (a generally non-selective compound), then the agent may be said to have selectivity for the inducible isoform.

i.v. or i.p. to the animals. As shown in FIG. 5, mercapto derivatives caused only a slight increase in mean arterial blood pressure (MAP), whereas the conventional reference compound L-NMA caused a pronounced and dose-dependent pressor response, thereby illustrating the selectivity of the mercapto derivatives.

EXAMPLE 3

Figure 6:
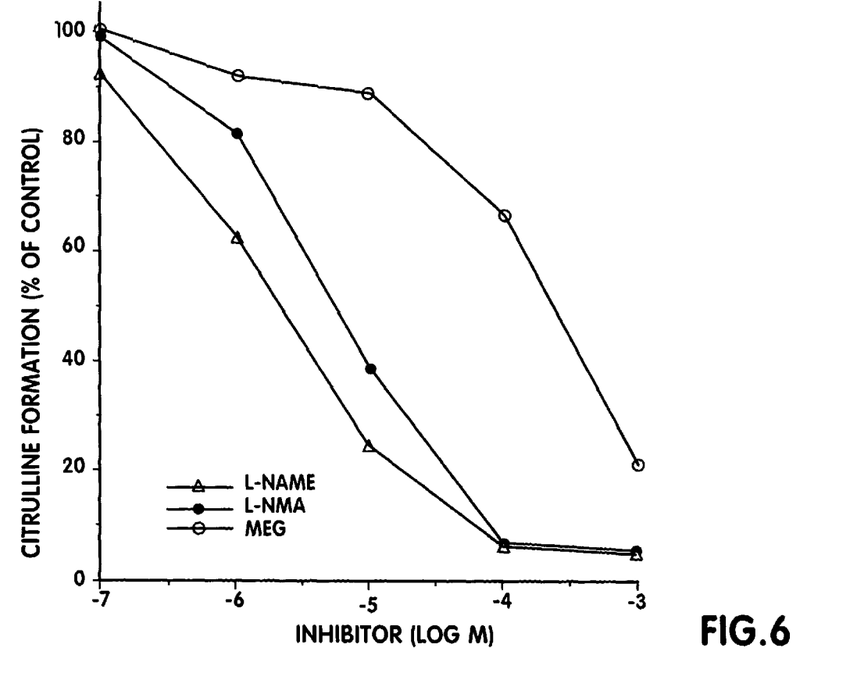
FIG. 6 is a graph of the effect of mercaptoethylguanidine (MEG), NG-methyl-L-arginine (L-NMA) and NG-nitro-L-arginine methyl ester (L-NAME) on citrulline formation by endothelial cell homogenates obtained from bovine aortae.

This is a further example of the relatively weak effect of mercaptoethylguanidine and related compounds on constitutive NOS activities (ecNOS and bNOS). ecNOS activity from bovine aorta was estimated as follows. The intimal surface of fresh bovine aortae was scraped in the presence of homogenation buffer composed of 50 mM Tris-HCl, 0.1 mM ethylenediamine tetraacetic acid (EDTA) and 0.1 mM ethyleneglycol bis (beta-aminoethyl ether) (EGTA). Conversion of [$^3$H]-L-arginine to [$^3$H]-L-citrulline was measured in the homogenates as follows: cell homogenate (50 $\mu$l) was incubated in the presence of [$^3$H]-L-arginine (10 $\mu$M, 5 kBq/tube), NADPH (2 mM), calmodulin (30 nM), tetrahydrobiopterin (5 $\mu$M) and calcium (2 mM) for 20 minutes at 37° C. in N-2-hydroxethyl piperazine-N-2-ethane sulfonic acid (HEPES) buffer (pH 7.5). Reactions were stopped by dilution with 1 ml of ice cold HEPES buffer (pH 5.5) containing EGTA (2 mM) and EDTA (2 mM). Reaction mixtures were applied to Dowex 50W (Na$^+$ form) columns and the eluted [$^3$H]-L-citrulline activity was measured by scintillation counting. bNOS activity was measured using similar methods in homogenates of whole rat brains. The dose dependent inhibition of ecNOS activity by mercaptoethylguanidine (MEG), when included in the incubation medium, was substantially less ($EC_{50}$=110 $\mu$M, n=6) than that of L-NMA ($EC_{50}$=5 $\mu$M, n=6) or L-NAME ($EC_{50}$=2 $\mu$M, n=6), thereby illustrating the isoform selectivity of the mercapto derivative (FIG. 6, Table 2). Similarly, S-methyl MEG and S-ethyl MEG were less potent on ecNOS while being relative potent inhibitors of iNOS activity (Table 2).

EXAMPLE 4

This Example illustrates a method for synthesizing mercaptoethylguanidine sulphate. Mercaptoethylamine hydrochloride (2 g) was dissolved in methanol (5 ml) and cooled in a salt/ice bath. A cold solution of potassium hydroxide (0.99 g) in methanol (10 ml) was added and the mixture stirred. After 1 hour, the solution was filtered and S-methylisothiourea (2 g) was added to 12 ml of the filtrate. The solution was stirred at room temperature (18° C.) for 16 hours under nitrogen. The solution then was filtered and ether was added to precipitate the crude product which was then recrystallized from an ether/ethanol mixture.

EXAMPLE 5

2-(Methylthio)ethylguanidine sulphate was prepared as follows: to a solution of 0.695 g S-methylisothiourea in 15 ml 90% methanol was added 0.456 g 2-(methylthio) ethylamine. The solution was stirred for 20 h at room temperature, filtered and the solvent removed in vacuo. The residue was crystallized from a mixture of methanol and ether.

EXAMPLE 6

2-(ethylthio)ethylguanidine sulphate was prepared using the procedure of example 5; however, 0.5 g of 2-(ethylthio) ethylamine was used instead of 2-(methylthio)ethylamine.

EXAMPLE 7

N-amidinylthiomorpholine sulphate was prepared as follows: thiomorpholine (3 ml) was added to a solution of 4.17 g S-methylisothiourea in 30 ml of 25% aqueous methanol and the solution was stirred overnight. The solvent was removed under reduced pressure and the residue taken up in warm methanol and filtered. The volume was reduced and the solution was left for 2 days after which the solid was collected.

EXAMPLE 8

N-amidinylthiazolidine sulphate was prepared as follows: thiazolidine (1g) was added to a solution of 1.56g S-methylisothiourea in 15 ml of 25% aqueous methanol and the solution was stirred overnight. The solvent was removed under reduced pressure and the residue recrystallized from methanol/water to give a white solid in low yield.

EXAMPLE 9

This example illustrates the effect of selected mercapto and seleno derivatives on nitrite production in J774.2 immunostimulated macrophages. The J774.2 mouse macrophage cell line was obtained from the ATCC and was cultured in DMEM with $4 \times 10^{-3}$ M L-glutamine and 10% fetal calf serum. Cells were cultured in 96-well plates with 200 μl culture medium until they reached 60–80% confluence. To induce iNOS, fresh culture medium containing *E.coli* LPS (10 μg/ml) and murine gamma-interferon (IFN)(50 U/ml) were added. Nitrite accumulation in the cell culture medium in the absence or presence of various inhibitors was measured after 24 hours. Nitrite production, an indicator of NO synthesis, was measured in the supernatant of J774.2 macrophages by the Greiss reaction as described in Example 1 above.

Figure 7:
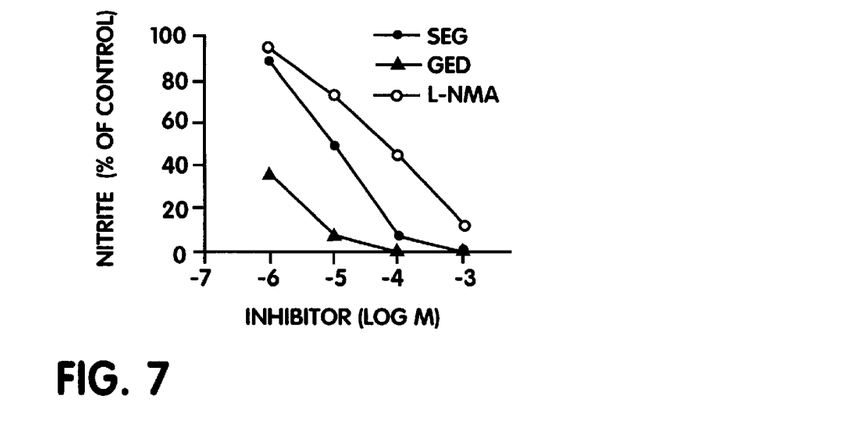
FIG. 7 is a graph of the effect of selenoethylguanidine (SEG), guanidinoethyldisulfide (GED) and NG-methyl-L-arginine (L-NMA) on nitrite production by immunostimulated J774 macrophages (N=6)

There was no detectable nitrite production by the J774.2 macrophages in the absence of immunostimulation. However, in the presence of IFN and LPS, nitrite concentration of the medium increased to 17±2 μM in the absence of inhibitors. Referring to FIG. 7 and Table 3, both SEG and GED caused a dose-dependent inhibition of nitrite production. Furthermore, the potency of each of these compounds was higher than the reference compound L-NMA. SEG had an $EC_{50}$ of 10 μM and GED had an $EC_{50}$ of 0.3 μM whereas the $EC_{50}$ value for L-NMA was 90 μM.

TABLE 3

EFFECT OF SELECTED COMPOUNDS ON NITRITE PRODUCTION IN IMMUNOSTIMULATED MACROPHAGES NITRITE (% OF CONTROL) USING

| Inhibitor Concentration (log M) | L-NMA | SEG | GED |
|---|---|---|---|
| −6.000 | 95.000 | 90.000 | 36.000 |
| −5.000 | 73.500 | 50.000 | 7.000 |
| −4.000 | 45.000 | 7.000 | 0.000 |
| −3.000 | 12.600 | 0.000 | 0.000 |

EXAMPLE 10

Figure 8:
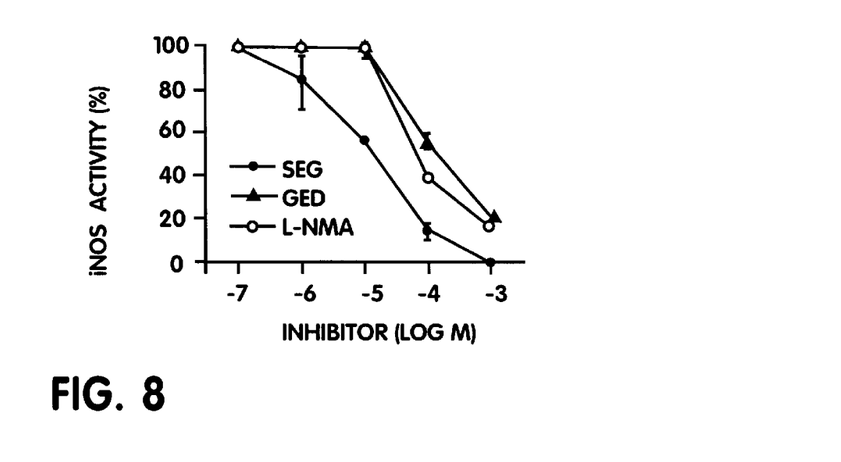
FIG. 8 is a graph of the effect of selenoethylguanidine (SEG), guanidinoethyldisulfide (GED) and NG-methyl-L-arginine (L-NMA) on iNOS activity in lung homogenate prepared from lungs obtained from rats treated with bacterial endotoxin (N=6)

This Example illustrates the effect of selected mercapto and seleno derivatives on iNOS activity in lung homogenates prepared from rats treated with endotoxin. Lungs were obtained from rats which had been treated with bacterial endotoxin (15 mg/kg IV) for three hours, and the lungs were subsequently homogenized. The homogenization buffer was composed of 50 mM tris-HCl, 0.1 mM EDTA, 0.1 mM EGTA and 1 mM phenylmethylsulfonyl chloride (pH 7.4). Cell suspensions were homogenized in the homogenization buffer on ice using a Tissue Tearor 985-370 homogenizer (BioSpec Products, Racine, Wis.). Referring to FIG. 8 and Table 4, GED and L-NMA are somewhat similar in their inhibitory effect on iNOS activity while SEG inhibits iNOS activity more strongly.

TABLE 4

EFFECT OF SELECTED COMPOUNDS ON iNOS ACTIVITY IN LUNG HOMOGENATES PREPARED FROM RATS TREATED WITH ENDOTOXIN iNOS ACTIVITY (%) USING

| Inhibitor Concentration (log M) | L-NMA | SEG | GED |
|---|---|---|---|
| −7.000 | 100.000 | 100.000 | 100.000 |
| −6.000 | 100.000 | 86.000 | 100.000 |
| −5.000 | 100.000 | 56.000 | 100.000 |
| −4.000 | 40.000 | 15.000 | 57.000 |
| −3.000 | 18.000 | 0.0000 | 22.000 |

EXAMPLE 11

This Example illustrates the effect of selected mercapto and seleno derivatives on ecNOS activity prepared from intimal scrapings of fresh bovine aortae. For a preparation rich in ecNOS, the intimate surface of fresh bovine aortae was scraped and homogenized. The homogenization buffer was composed of 50 mM tris-HCL, 0.1 mM EDTA, 0.1 mM EGTA and 1 mM phenylmethylsulfonyl chloride (pH 7.4). Cell suspensions were homogenized in the homogenization buffer on ice using a Tissue Tearor 985-370 homogenizer (BioSpec Products, Racine, Wis.). Conversion of $[^3H]$-L-arginine to $[^3H]$-L-citrulline was measured in the homogenates as described in Example 3 above.

Figure 9:
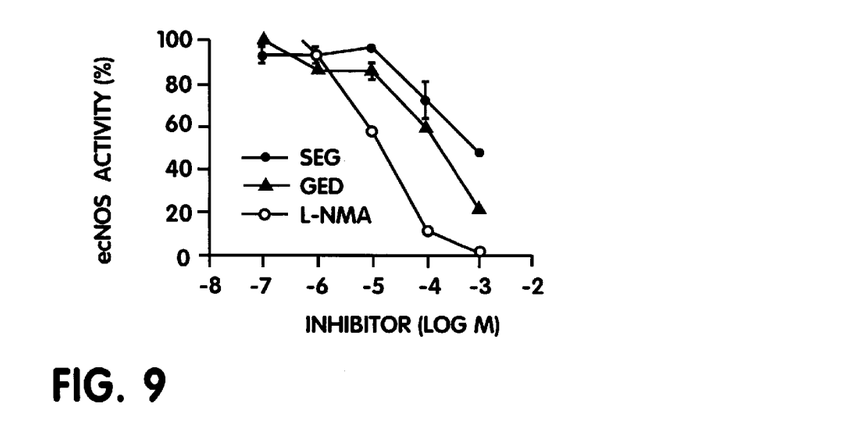
FIG. 9 is a graph of the effect of selenoethylguanidine (SEG), guanidinoethyldisulfide (GED) and NG-methyl-L-arginine (L-NMA) on ecNOS activity prepared from intimal scrapings of fresh bovine aortae (N=6)

Referring to FIG. 9 and Table 5, SEG and GED inhibited ecNOS activity less strongly than the L-NMA. Furthermore, comparing FIGS. 8 and 9 and Tables 4 and 5, the $EC_{50}$ for SEG on iNOS (10 μM) was significantly less than the $EC_{50}$ for SEG on ecNOS (600 μM). In addition, the $EC_{50}$ for GED on iNOS (200 μM) was significantly less than the $EC_{50}$ of GED on ecNOS (630 μM). These $EC_{50}$ values further demonstrate the relative selectivity of SEG and GED for iNOS.

TABLE 5

EFFECT OF SELECTED COMPOUNDS ON ecNOS ACTIVITY PREPARED FROM THE INTIMAL SCRAPINGS OF FRESH BOVINE AORTAE
ecNOS ACTIVITY USING

| Inhibitor Concentration (log M) | L-NMA | SEG | GED |
| --- | --- | --- | --- |
| −7.000 | 117.000+ | 93.000 | 99.000 |
| −6.000 | 93.000 | 93.000 | 86.000 |
| −5.000 | 58.000 | 97.000 | 86.000 |
| −4.000 | 12.000 | 73.000 | 60.000 |
| −3.000 | 2.000 | 48.000 | 23.000 |

+ result likely due to experimental error

EXAMPLE 12

Figure 10:
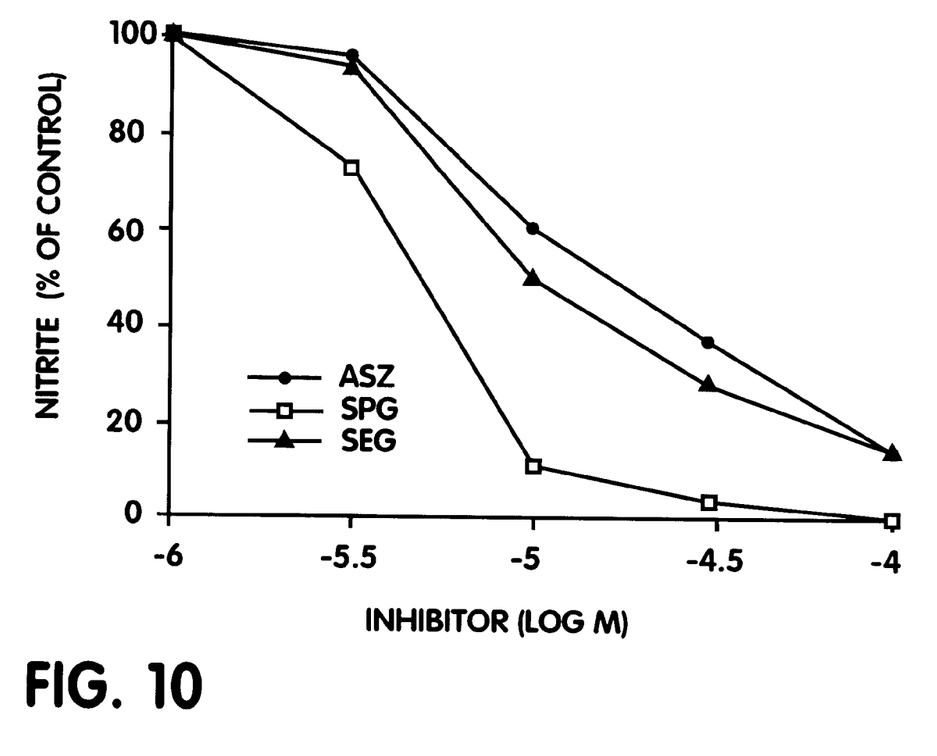
FIG. 10 is a graph of the effect of 2-aminoselenazoline (ASZ), selenopropylguanidine (SPG) and selenoethylguanidine (SEG) on nitrite production by immunostimulated J774 macrophages (N=6).

This Example illustrates the effect of selected seleno derivatives on endotoxin-induced nitrite formation in J774.2 macrophages. The mouse macrophage cell line J774.2 obtained from the ATCC was cultured in DMEM with $4 \times 10^{-3}$ M L-glutamine and 10% fetal calf serum. Cells were cultured in 96-well plates with 200 μl culture medium until they reached 60–80% confluence. To induce iNOS, fresh culture medium containing *E.coli* LPS (10 μg/ml) and murine gamma-interferon (IFN)(50 U/ml) were added. Nitrite accumulation in the cell culture medium in the absence or presence of various inhibitors was measured after 24 hours. There was no detectable nitrite production by the J774.2 macrophages in the absence of immunostimulation. However, in the presence of IFN and LPS, nitrite concentration of the medium increased to 17±2 μM in the absence of inhibitor. Referring to FIG. 10 and Table 6, ASZ, SEG and SPG dose-dependently inhibited nitrite production.

TABLE 6

EFFECT OF SELECTED COMPOUNDS ON NITRITE PRODUCTION IN IMMUNOSTIMULATED MACROPHAGES
NITRITE (% OF CONTROL) USING

| Inhibitor Concentration (log M) | ASZ | SEG | SPG |
| --- | --- | --- | --- |
| −6 | 100 | 100 | 100 |
| −5.5 | 96 | 94 | 73 |
| −5 | 60 | 50 | 11 |
| −4.5 | 37 | 28 | 4 |
| −4 | 14 | 14 | 0 |

The detailed description of the invention presented above is provided by way of illustration, and it is not intended to limit the scope of the invention which is to be determined by the following claims.

What is claimed is:

1. A pharmacologically acceptable composition for inhibiting nitric oxide synthase in a mammal, comprising:
   a compound having a formula selected from the group consisting of:

and or a salt thereof, wherein $R_1$ is H, alkyl, alkenyl, phenyl, alkylene, alkenylene, or phenylalkylene or a substituted derivative thereof;

When $R_1$ is alkylene or alkenylene, $R_1$ optionally may be joined to either of the amidino Ns, to Z or to X of the above formula containing $R_1$ to form a 5-, 6- or 7-membered heterocyclic ring, with the proviso that when $R_1$ is attached to Z, Z is alkylene or alkenylene or a substituted derivative thereof, and, when $R_1$ is attached to X, X is either $CR_5$ or N;

$R_2$, $R_3$, $R'_2$ and $R'_3$ are independently H, lower alkyl, alkenyl, alkylene, alkenylene, amino, phenyl or phenylalkylene, or a substituted derivative thereof;

When $R_2$ or $R'_2$ is alkylene or alkenylene, $R_2$ or $R'_2$ optionally may be joined to the imino N residing on the adjacent amidino C to form a 5- or 6-membered heterocyclic ring;

Z and Z' are independently alkylene, alkenylene, cycloalkylene or cycloalkenylene, or a substituted derivative thereof;

When $R_2$, $R_3$, $R'_2$ or $R'_3$ is alkylene or alkenylene, $R_2$, $R_3$, $R'_2$ or $R'_3$ optionally may be joined to the adjacent Z or Z' to form a 5- or 6-membered heterocyclic ring including N, C and not more than one atom of O or S, with the proviso that said heterocyclic ring optionally being substituted with a lower alkyl, alkoxy, halo, hydroxy or amino;

X is N, $NR_4$, O, $CR_5$ or $CR_4R_5$;

X' is N, $NR'_4$, O, $CR'_5$ or $CR'_4R'_5$;

Y is Se;

$R_4$ and $R'_4$ are independently H, alkyl, thioalkylene or thioesteralkylene;

$R_4$ and $R'_5$ are independently H, alkyl, alkylene, alkenylene, thioalkylene, thioesteralkylene, amino or carboxyl;

When $R_4$ or $R'_4$ is alkylene, alkenylene, thioalkylene, or thioesteralkylene, $R_4$ or $R'_4$ optionally may be joined to $R_2$, $R_3$, $R'_2$ or R'3 to form a 5- or 6-membered heterocyclic ring including N, C and not more than one atom of 0 or S, with the proviso that $R_2$, $R_3$, $R'_2$ and $R'_3$ are independently alkylene, alkenylene, amino, phenyl, phenylalkylene, or a substituted derivative thereof wherein the substituted derivative is lower alkyl or halo;

and a pharmaceutically acceptable carrier, said mercapto derivative present in said composition in an effective amount to inhibit nitric oxide synthase in said mammal.

2. The composition of claim 1 wherein said substituted derivative of $R_1$ is selected from the group consisting of one or more of alkoxy, halo, hydroxy, amino and nitro.

3. The composition of claim 1 wherein said substituted derivative of $R_2$, $R_3$, $R'_2$ or $R'_3$ is independently selected from the group consisting of lower alkyl and halo.

4. The composition of claim 1 wherein said $R_4$, $R_5$, $R'_4$ or $R'_5$ thioalkylene has a formula $[-(CH_2)_n-SH]$ where n is independently 1 to 4.

5. The composition of claim 1 wherein said $R_4$, $R_5$, $R'_4$ or $R'_5$ thioesteralkylene has a formula $[-(CH_2)_n-S-R]$ where $R_6$ is independently a lower alkyl and n is independently 1 to 4.

6. The composition of claim 1 wherein said substituted derivative of Z or Z' is independently selected from the group consisting of alkoxy, halo, hydroxy, amino and nitro.

7. The composition of claim 1 wherein $R_1$ is selected from the group consisting of H and lower alkyl, $R_2$ is H, $R_3$ is H, $R'_2$ is H, $R'_3$ is H, X is $NR_4$, X' is $NR'_4$, $R_4$ and $R'_4$, are independently selected from the group consisting of H, methyl and ethyl, and Z and Z' are independently alkylene.

8. The composition of claim 1 wherein $R_1$ is H, $R_2$ is H, $R_3$ is H, $R'_2$ is H, $R'_3$ is H, X is $NR_4$, X' is $NR'_4$, $R_4$ is H, $R'_4$ is H and Z and Z' are independently a $C_{1-6}$ alkylene.

9. The composition of claim 1 wherein said compound is selected from the group consisting of mercaptoethylguanidine, mercaptopropylguanidine, S-methyl-mercaptoethylguanidine, S-methyl-mercaptopropylguanidine, selenoethylguanidine, selenopropylguanidine and guanidinoethyldisulfide.

10. The composition of claim 1 wherein said compound selectively inhibits inducible nitric oxide synthase.

11. The composition of claim 1 wherein said compound is present in an amount sufficient to treat a condition where there is an advantage in inhibiting the nitric oxide synthase enzyme.

12. The composition of claim 11 wherein said condition is selected from the group consisting of circulatory shock, systemic inflammatory response syndrome, therapy with cytokines, therapy with cytokine-inducing agents, transplantation, transplant rejection, local inflammatory responses, systemic inflammation, autoimmune diseases, adult respiratory distress syndrome, arthritis, rheumatoid arthritis, diabetes mellitus, ileitis, ulcerative colitis, Crohn's disease, asthma, periodontitis, nephrosis, chronic demyelinating diseases of the nervous system, multiple sclerosis, AIDS-related complications, Alzheimer's disease, ischemic heart disease, cardiomyopathy, adrenal insufficiency, hypercholesterolemia, atherosclerosis, bone diseases associated with increased bone resorption, pre-eclampsia, eclampsia, uremic complications, chronic liver failure, stroke, cerebral ischemia, and cancer.

13. The composition of claim 11 wherein said condition is selected from the group consisting of systemic inflammatory response syndrome and circulatory shock.

14. The composition of claim 1 formulated for oral, rectal, nasal, topical, buccal, sub-lingual, vaginal, parenteral, intramuscular, sub-cutaneous, intravenous, inhalation or insufflation administration.

15. The composition of claim 1 formulated for oral administration, said carrier including an ingredient selected from the group consisting of a binding agent, filler, lubricant, disintegrant, wetting agent, inert diluent, surface active agent, dispersing agent, suspending agent, emulsifying agent, edible oil, flavoring agent and mixtures thereof.

16. The composition of claim 1 formulated for topical administration in the mouth, said carrier including an ingredient selected from the group consisting of a flavor, sucrose, acacia, tragacanth, gelatin, glycerin and mixtures thereof.

17. The composition of claim 1 formulated for nasal administration, said carrier including an ingredient selected from the group consisting of a dispersing agent, solubilizing agent, suspending agent and mixtures thereof.

18. The composition of claim 1 formulated for administration by inhalation, said carrier including a propellant.

19. The composition of claim 18 wherein said propellant is selected from the group consisting of dichlorodifluoromethane, trichlorofluoromethane, dichlorotetrafluoroethane, carbon dioxide and and mixtures thereof.

20. The composition of claim 1 formulated for administration by inhalation or insufflation, said carrier including an ingredient selected from the group consisting of lactose, starch and mixtures thereof.

21. The composition of claim 1 formulated for parenteral administration, said carrier including an ingredient selected from the group consisting of an anti-oxidant, buffer, bacteriostat, suspending agent, thickening agent, saline, water and mixtures thereof.

22. The composition of claim 1 formulated for rectal administration, said carrier including an ingredient selected from the group consisting of cocoa butter, polyethylene glycol and mixtures thereof.

23. The composition of claim 1 formulated to include an ingredient selected from the group consisting of an antimicrobial agent, an immunosuppressant, a preservative and mixtures thereof.

24. The composition of claim 1 formulated for administration at a dose of from about 5 mg to about 17.5 g/day of said compound.

25. The composition of claim 24 formulated for administration at a dose of from about 5 mg to about 10 g/day of said compound.

26. The composition of claim 25 formulated for administration at a dose of from about 100 mg to about 3 g/day of said compound.

* * * * *

UNITED STATES PATENT AND TRADEMARK OFFICE
CERTIFICATE OF CORRECTION

PATENT NO. : 5,985,917
DATED : November 16, 1999
INVENTOR(S) : Garry J. Southan, et al.

It is certified that error appears in the above-identified patent and that said Letters Patent is hereby corrected as shown below:

Column 2,
Line 13, delete "Szaboet al." and insert therefore -- Szabo et al. --.

Column 5,
Line 66, delete "R'4" and insert therefore -- $R'_4$ --.

Column 6,
Line 7, delete "addition" and insert therefore -- additional --.

Column 14,
Line 61, delete "HCL" and insert therefore -- HC1 --.

Claim 1,
Lines 36 and 37, delete "$CR_4R'_5$; Y is Se" and insert therefore -- $CR'_4R'_5$; Y is S --.
Line 39, delete "$R_4$ and $R'_5$" and insert therefore -- $R_5$ and $R'_5$ --.
Line 45, delete "R'3" and insert therefore -- $R'_3$ --.

Claim 5,
Line 2, delete "-S-R]" and insert therefore -- -S-$R_6$] --.

Claim 19,
Line 4, delete "and and", and insert therefore -- and --.

Signed and Sealed this

Sixth Day of November, 2001

*Attest:*

*Attesting Officer*

NICHOLAS P. GODICI
*Acting Director of the United States Patent and Trademark Office*